United States Patent [19]

Pfister et al.

[11] Patent Number: 4,951,657
[45] Date of Patent: Aug. 28, 1990

[54] HEAT SEALABLE MEMBRANE FOR TRANSDERMAL DRUG RELEASE

[75] Inventors: William R. Pfister, Bay City; Chi-Long Lee; Gerald A. Gornowicz, both of Midland, all of Mich.

[73] Assignee: Dow Corning Corporation, Midland, Mich.

[21] Appl. No.: 184,750

[22] Filed: Apr. 22, 1988

[51] Int. Cl.⁵ ............................................. A61K 9/00
[52] U.S. Cl. ................................. 128/156; 604/890.1
[58] Field of Search ............................. 604/304–307, 604/896.1; 128/155, 156; 424/443, 447–449

[56] References Cited

U.S. PATENT DOCUMENTS

| | | | |
|---|---|---|---|
| 3,279,996 | 10/1966 | Long, Jr. et al. | 424/424 |
| 3,529,035 | 9/1970 | Lamoreaux | 128/156 |
| 3,598,122 | 8/1971 | Zaffaroni | 604/304 |
| 4,559,054 | 12/1985 | Bruck | 604/304 |
| 4,638,043 | 1/1987 | Szycher et al. | 424/448 |
| 4,675,361 | 6/1987 | Ward, Jr. | 525/453 |
| 4,686,137 | 8/1987 | Ward, Jr. | 525/453 |
| 4,747,845 | 5/1988 | Karol | 424/447 |
| 4,814,173 | 3/1989 | Song et al. | 424/449 |
| 4,814,184 | 3/1989 | Aguadisch et al. | 424/443 |
| 4,838,253 | 6/1989 | Brassington | 604/304 |
| 4,840,796 | 6/1989 | Sweet et al. | 424/448 |

OTHER PUBLICATIONS

Robert S. Ward, Jr. and Emery Nyilas, Production of Biomedical Polymers I. Silicone/Urethane Synergy in Avcothane$^R$ Elastomers, 1978, p. 224.

*Primary Examiner*—Stephen C. Pellegrino
*Assistant Examiner*—Sharon Rose
*Attorney, Agent, or Firm*—Allen O. Maki

[57] ABSTRACT

A transdermal drug delivery system, is provided which includes, in combination, an impermeable backing member, a release rate controlling membrane, and, a reservoir containing a medicinally active ingredient; the improvement in such system is based on the fact that said membrane is heat and pressure sealed to said backing without the use of a separate adhesive and is formed of a substantially linear block copolymer which is a reaction product of an amino functional polydiorganosiloxane which forms soft segments in said reaction product and a diisocyanate which forms "hard" segments, said copolymer having a glass transition temperature between 50° C. and 200° C. said soft segments comprising from 60 to 90 percent by weight, based on the weight of said copolymer.

10 Claims, No Drawings

HEAT SEALABLE MEMBRANE FOR TRANSDERMAL DRUG RELEASE

BACKGROUND OF THE INVENTION

1. Field of the Invention

This invention relates to the controlled release of medications or active substances which are administered transdermally. More particularly, this invention relates to a membrane for controlling the release of at least one drug or medication, which membrane can be fabricated or incorporated into a composite structure by heat sealing.

2. Description of the Prior Art

Rate controlling membranes have been used as a component of transdermal drug delivery devices. Silicone elastomers have often been employed in such applications because of the permeability of such elastomers to a number of drugs and medications. The use of silicone rubbers in such applications is limited commercially, however, because it is difficult to economically attach the cured membrane material to the other materials from which such devices are constructed. Such membranes are designed to control the rate at which these medications are released through the membrane into the skin of the patient. A reservoir containing the medication is sometimes placed between the membrane and an impermeable backing material, and a pressure sensitive adhesive applied over all or a portion of the membrane to attach the composite transdermal drug delivery device to the skin of the patient.

Depending upon the type of drug or medication and the desired release rate, the rate controlling portion of the device that is permeable to the medication has hithertofore been a layer of non-porous material such as ethylene vinyl acetate copolymer or crosslinked silicone rubber, or a porous film. The medication permeates through the matrix, if any, that forms the drug containing reservoir, the membrane, and the pressure sensitive adhesive, if the latter is positioned between the drug containing reservoir and the skin. The exposed surface of the pressure sensitive adhesive is generally covered by a release liner which is removed and discarded when the device is used.

A number of patents disclose the general concept of transdermal drug delivery devices. Representative of these is U.S. Pat. No. 3,598,122 to Zaffaroni. That patent discloses the use of silicone rubber as a membrane, but does not teach the use of the thermoplastic copolymers of the present invention.

In addition to lacking heat sealability, membranes of silicone rubber such as those disclosed in the prior art tend to be insufficiently permeable to provide the desired release rate of a medication particularly in the case of medications which are hydrophilic or of an ionic nature. Films and coatings formed from the hydrophobic silicone polymers are not preferred in such applications because of the limited permeability of such materials through the polymers which are generally of a hydrophobic nature. In some cases a matrix containing the drug to be administered is employed without a separate rate controlling membrane. Such embodiments are shown in U.S. Pat. No. 4,655,767 to Woodard et al.

U.S. Pat. No. 4,686,137, which issued to Ward and Riffle on Aug. 11, 1987, discloses the use as an additive in base polymers of small amounts of polyurethane urea-silicone block copolymers consisting essentially of a "hard" segment that is preferably a polyurethane formed from the reaction of diphenylmethane diisocyanate with a diol, and a "soft" segment having both hydrophilic and hydrophobic portions. The hydrophobic portion of the soft segment can be a polymeric tetraalkylene oxide, such as polytetramethylene oxide (PTMO), a polydialkylsiloxane, or a mixture of these two polymers, and the preferred hydrophilic segment is polyethylene oxide (PEO). These copolymers are combined with a base polymer, such as a polyurethane, and a suitable solvent to form films suitable for use as wound dressings or semipermeable membranes and as coating compositions for textile materials. As disclosed, however, the copolymers contain only a very minor weight percentage of silicone segments, and constitute only a small fraction of the weight of the base polymer, and thus would not be the equivalent of the polymers of this invention for use as a rate controlling membrane in a drug delivery device.

It has been reported that various copolymers of polysiloxanes can be used in drug delivery applications. See, for example, Ulman et al, *Proceed. Intern. Symp. Control Rel. Bioact. Mater.*, 13: 228-229 (1986). However, even in light of these publications there has remained a need for a heat sealable membrane material which can be tailored to maximize the permeation therethrough of a wide variety of drugs.

An objective of this invention is to provide materials for membranes that enable the migration therethrough of a variety of medications and which can be heat sealed onto a variety of substrates or backings. By elimination of the need of using adhesives between the silicone membrane and other parts of the device (e.g. the backing), which adhesives might alter the rate of drug delivery or present either health hazards or problems of incompatability with the medication being administered, a number of problems encountered with the prior art are eliminated. Also an important advantage in the ability to employ commercially feasible assembly methods in manufacture of drug delivery devices is attained.

SUMMARY OF THE INVENTION

The present inventors discovered that membranes formed from certain members of the broad class of segmented block copolymers are unique by virtue of (1) their high permeability to the ingredients of various mixtures of medications including those of a hydrophilic type, (2) their resistance to swelling and/or degradation by ingredients of the medications, (3) their biocompatability, and, (4) their ability to be fabricated into composite devices by the use of heat and pressure without adhesives.

The present copolymers comprise a hard segment which comprises an organic diisocyanate or is derived from the reaction of an organic diisocyanate with a diol and a soft segment (or oligomer) containing at least one polydiorganosiloxane unit, preferably a polydimethylsiloxane (PDMS) unit, as a hydrophobic portion and, optionally, one or more oxyethylene units as a hydrophilic portion. Films formed from these copolymers are particularly useful for controlling the release of drugs and medications to the skin of a patient to whom the desired drug is being administered.

Briefly summarized, the present invention provides, in a transdermal drug delivery system, which includes in combination: (a) an impermeable backing member; (b) a drug permeable membrane (which can be a release rate controlling membrane), and; (c) a reservoir containing a medicinally active ingredient; the improvement characterized by the fact that said membrane is heat and pressure sealed to said backing without the use of a separate adhesive and comprises a substantially linear block copolymer which is a reaction product of a polydiorganosiloxane (which is provided with end groups that are reactive with isocyanate groups, e.g., —$RNH_2$, —OH, or —SH) which form "soft" segments in said reaction product and a diisocyanate which forms "hard" segments, said copolymer having a hard segment glass transition temperature between 50° C. and 200° C. said soft segments comprising from 60 to 90 percent by weight, based on the weight of said copolymer, the average molecular weight of said copolymer being between 50,000 and 500,000.

DETAILED DESCRIPTION OF THE INVENTION

This invention provides an membrane material for controlling the release from a reservoir to the skin or mucosa of a patient of at least one drug or medication, where (1) the rate controlling membrane comprises a heat sealable layer of a solid polymer having a glass transition temperature between about 50° and 200° C., where said layer is inert with respect to and permeable with respect to said drug or medication, (2) said membrane is heat sealed without the use of other adhesives to a backing, and (3) said membrane comprises a layer 0.01 to 1 mm. thick of a substantially linear block copolymer comprising from 10 to 40 weight percent of "hard" segments consisting essentially of polyurethane or polyurea units derived from an organic diisocyanate and, if desired, an alkylene diol, and from 60 to 90 weight percent of "soft" segments comprising from 20 to 90 percent by weight, based on the weight of said copolymer, of a hydrophobic portion consisting essentially of at least one polydiorganosiloxane unit and from 0 to 70 percent by weight, based on the weight of said copolymer, of a hydrophilic portion consisting essentially of at least one polyalkylene oxide unit. The presence and amount of hydrophilic portions is dependent on the nature, particularly the hydrophilicity or lipophilicity of the drug which is intended to be delivered through the membrane.

This invention also provides an improved method for forming a composite drug delivery device, by heat sealing onto a backing (which may be either a drug impermeable polymer, metal foil, or the like) a layer of a polymeric material that is from 0.01 to 1 mm. thick and permeable to said drug where the drug or medication is positioned between the backing and a membrane formed from said polymeric material comprising the substantially linear block copolymers described in the preceding paragraph.

The drug permeable membrane (which may be rate controlling) for releasing the medicinal ingredients from the drug-containing reservoir of the drug delivery device is a drug permeable, heat sealable, thermoplastic layer of a diorganosiloxane/polyurethane segmented or block copolymer. The copolymer can optionally contain blocks of polyalkylene oxide molecules if it is desired to increase the hydrophilicity of the element. The term "polyurethane" as used herein is intended to refer to not only polyurethanes, but also, polyureas and polyurethane-ureas, all of which are commonly referred to in the art generically as polyurethanes.

The molecules of block copolymer that constitute the drug permeable membranes of the present invention contain at least one segment of a "hard" polymer and at least one segment of a "soft" polymer. It is understood in the art that the terms "hard" and "soft" as applied to segments of block copolymers refer to the relative glass transition temperatures ($T_g$) of the two segments. The hard segments have a higher $T_g$ than the soft segments.

The hard segment of the present copolymers is a polyurea or polyurethane derived from an organic diisocyanate and optionally a low molecular weight diol or diamine, sometimes referred to as a chain extender. Any of the available aliphatic, aromatic or cycloaliphatic diisocyanates can be used to prepare the polyurea or polyurethane portion of these copolymers. Preferred diisocyanates include but are not limited to p-toluene diisocyanate (TDI), 4,4'-diphenyl methane diisocyanate (MDI) and 4,4'-dicyclohexylmethyldiisocyanate ($H_{12}MDI$), and isophorone diisocyanate (IPDI).

The chain extender portion of the polyurethane can be any of the available aliphatic diols or diamines containing from 2 up to about 10 carbon atoms. Diols containing from 2 to 4 carbon atoms are preferred.

The hard segment constitutes from 10 to 40 weight percent of the copolymer, preferably from 15 to 35 weight percent, and the molar ratio of hard segment (diisocyanate and aliphatic diol units) to soft segments (polydiorganosiloxane and polyalkylene oxide units) is from 3/1 to 7/1, preferably about 5/1. The soft segment of the present copolymers may include a hydrophilic and a hydrophobic portion. The hydrophobic portion of the copolymer molecules consists essentially of at least one sequence of from 15 to about 100 diorganosiloxane units, and these sequences constitute from 20 to 90 weight percent, preferably from 40 to 80 weight percent, of the copolymer. Methods for preparing functionally substituted polydimethylsiloxanes, or other polydiorganosiloxanes, and copolymerizing these polymers with diisocyanates and other organic monomers are known in the art and do not form part of this invention. See, for example, Gornowicz et al U.S. Pat. No. 4,631,629.

The hydrophilic portion of the soft segment consists essentially of at least one sequence per copolymer molecule of from 5 to 75 oxyethylene units, which can be present as part of the linear portion of the copolymer or as pendant groups attached to the diorganosiloxane units. The oxyethylene units constitute from 0 to 70 weight percent of the copolymer.

The molecular weight of the copolymer is not considered critical to the ability of the copolymer to function as the rate-controlling element for release of medications in accordance with the present invention. The optimum molecular weight range for a given copolymer will be determined by the desired physical properties of the copolymer, such as tensile strength, elongation and tear strength, and particularly the glass transition temperature of the hard segment of the copolymer. The weight average molecular weight is preferably from 30,000 to about 500,000. If the rate-controlling element is prepared from a heat sealable copolymer of this invention, the weight average molecular weight of the copolymer is typically in the range of from 50,000 to about 200,000 to facilitate heat sealing at temperatures which are feasible from a commercial manufacturing viewpoint.

Methods for preparing dimethylsiloxane/polyurethane urea-oxyethylene copolymers are described in patents and other literature, see for example, Tyagi et al, "Segmented organosiloxane copolymers", Polymer, Vol. 25, pp 1807-1816. In accordance with a preferred method, a liquid amino functional (end blocked) polydiorganosiloxane containing from 15 to about 100 repeating units per molecule, wherein the amino endblocking unit is, for example:

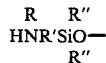

and is at the two terminal positions, is reacted with the organic diisocyanate and a polyalkylene oxide by heating the mixture in the presence of a suitable catalyst. The aliphatic diol or other chain extender that forms part of the hard segment is then added to the reaction mixture and heating continued for an additional 2 to 16 hours. The reaction is preferably conducted under an inert atmosphere such as nitrogen using as the reaction medium an organic liquid such as toluene, tetrahydrofuran (THF) or a mixture of toluene and more polar solvents such as tetrahydrofuran or N,N dimethlyformamide (DMF) that will dissolve all of the reactants and the resultant copolymer. The preferred polydiorganosiloxane is polydimethylsiloxane because of high drug permeability, biocompatability, cost and availability.

The substituents represented by R and R" in the preceding formula are monovalent hydrocarbon radicals and R' represents an alkylene radical. Each of the radicals R, R' and R" may be the same or different.

Membranes or films of the present copolymers control the rate at which the medicinal ingredients of drug compositions are released from a reservoir into the skin of a patient. Depending upon the release rate of a particular drug through the copolymer, those skilled in the art can fabricate a drug delivery device designed to suit the particular application by altering the hydrophilicity/hydrophobicity of the copolymer to tailor it to the specific drug.

The present block copolymers are thermoplastic and can be processed to form films using any of the known techniques for fabricating thermoplastic organic polymers. These techniques include but are not limited to pressing, blowing, calendaring, and extrusion of bulk copolymers and dissolving the copolymers to form solutions that are then applied to a suitable substrate to form coatings as thin as 0.01 mm. Depending upon the desired release rate and the design of the drug delivery device the film or layer can be from 0.01 up to 1 mm. in thickness. The copolymer can be in the form of a self-supporting film or can be extruded and/or calendared directly onto a substrate which will form the backing for a drug delivery device with the drug sandwiched between.

Membranes of the present invention can be incorporated into a drug delivery device by heat sealing the membrane over a drug containing reservoir which is sandwiched between the membrane and a backing material, which may be, for example, plastic or metal foil. The membrane is positioned with the periphery therof extending beyond the perimeter of the reservoir. If desired, the membrane may be heat sealed onto the backing by applying heat and pressure, for example using platen presses or rotary dies. A layer of pressure sensitive adhesive is then applied either over the entire exposed surface of the membrane or at least the periphery thereof.

The specific drugs used are not critical to this invention and as used herein the term "drug" is to be construed in its broadest sense as a material which is intended to produce some beneficial effect on the organism to which it is applied. As used herein, a drug in its acid or basic form is considered to be oleophobic if the solubility of the drug in mineral oil is less than about 100 mg/g. A drug is considered to be "highly polar" when the percent ionization of the drug in an aqueous drug reservoir is at least about 95%. This occurs when the pKa of the drug differs from the pH of the reservoir by an absolute value of at least 1.3. The pKa of a drug is the pH of an aqueous solution in which 50% is in the unionized base or acid form. Since physiological pH of the skin is in the range of approximately 5.5-7.2; the pKa for acidic drugs according to this invention is lower than about 4.2 and for basic drugs, higher than 8.5. Representative drugs meeting these criteria include, without limitation, acidic drugs such as the sodium or other salts of indomethacin, acetazolamide, methazolamide, and acetylsalisylic acid, for example, and salts or acid salts of basic drugs such as naltrexone HCl, naloxone HCl, nalbuphine HCl, phenylephrine HCl, chlorpheniramine maleate, phenylpropanolamine HCl, clonidine HCl, dextromethophan HBr, atropine sulfate, fentanyl citrate, apomorphine sulfate, propranolol HCl, lidocaine HCl, tetracycline HCl, oxytetracycline HCl, tetracaine HCl, dibucaine HCl, terbutaline sulfate, and brompheniramine maleate, for example. Polar drugs generally require the incorporation of a hydrophilic component into the soft blocks of the copolymer whereas lipophilic (oleophilic) drugs will generally be transmitted through copolymers which do not contain such a component.

The following examples describe preferred embodiments of the present copolymers. The examples should not be interpreted as restricting the scope of the invention as defined in the accompanying claims. Unless otherwise specified, all parts and percentages in the examples are by weight.

EXAMPLE 1

Urethane-urea copolymers were prepared using procedures outlined in U.S. Pat. No. 4,631,629. The mole ratio of diisocyanate to low molecular weight alkylenediol, chain extender to aminoalkyl endblocked (PDMS) plus polyalkylene oxide (if used) was kept at 3/2/1.

Preparation of PDMS-PTMO Urethane (Copolymer 6)

($H_{12}$MDI) (106 g, 0.795 eq) and toluene (375 g) were put in a 3 liter. 3-neck flask equipped with an air stirrer, reflux condenser, addition funnel and nitrogen atmosphere. Methylamino-i-butyl endblocked PDMS (240.5 g, 0.14 eq) in toluene (700 g) was added slowly over a 30 minute period. A solution of PTMO (133.8 g, 0.125 eq) in toluene (133.8 g) and 0.3 ml of dibutyltin dilaurate (DBTDL) (10% solution) were added and the temperature was increased to 100° C. After 1 hour 1,4-butanediol (BD) (23.85 g, 0.53 eq) was added. Toluene (100 g) was used to rinse the addition funnel. Reaction was heated at 100° C. overnight until all the isocyanate had reacted. The solution was poured into baking dishes. After it cooled to room temperature it formed a soft rubber. The rubber was cut into small pieces and the solvent was permitted to evaporate in a hood. Residual solvent was removed in a vacuum oven to give Copolymer 6.

Preparation of PDMS-PEO Urethane (Copolymer 7)

($H_{12}MDI$) (106 g, 0.795 eq) and toluene (300 g) were charged to a 3 liter. 3 neck flask equipped with an air stirrer, reflux condenser, addition funnel and nitrogen atmosphere. Methylamino-i-butyl endblocked PDMS (30 dp) (218.2 g, 0.185 eq) dissolved in toluene (600 g) was added over a period of 30 minutes. Dry Carbowax 1450 (63.8 g, 0.08 eq) in toluene (63.8 g) and DBTDL (0.3 ml of 10% solution in toluene) were added and the reaction was heated at 100° C. for one hour. 1,4-Butanediol (23.85 g, 0.53 eq) was added and the reaction was heated at 95° C. overnight. The hot solution was poured into baking dishes. Upon cooling the product, a swollen elastomer, was cut into small pieces and most of the solvent was permitted to evaporate in a hood. The remaining solvent was removed in a vacuum oven at 100° C. to give copolymer 7.

Preparation of MDI Urethanes (Copolymer 4)

(MDI) (250 g, 2.0 eq) and toluene were put in a 5 liter flask equipped with an air stirrer, reflux condenser, addition funnel and nitrogen atmosphere. Methylamino-i-butyl endblocked PDMS (389.5 g) in toluene (816 g) and DBTDL (0.3 ml of 10% solution) was added slowly. An exothermic reaction increased the temperature from 25° C. to 33° C. The temperature was increased to 96° C. and BD (60 g, 1.33 eq) was added. The temperature increased from 96° to 112° C. The reaction became cloudy and 800 ml of DMF was added to give a clear solution. After all the isocyanate had reacted the solvents were removed in a vacuum oven.

The other copolymers referred to in Tables I-IV were prepared using similar procedures, utilizing the proportions of ingredients indicated in the table.

EXAMPLE 2. HEAT SEAL TESTS

About 5 g of copolymer was put in a 0.254 mm chase with calendered Teflon release sheets. These were placed in steam heated mold at 165° C. Initially, the pressure was increased slowly, 1 to 35 MPa, to allow the copolymer time to flow. Then the pressure was increased rapidly to 100 to 140 MPa for about 2 minutes. The sample was cooled to less than 50° C. This first membranes usually contained wrinkles. The membrane was remolded with new Teflon release sheets to give a smooth, uniform membrane approximately 0.25 mm thick.

Qualitative heat seal tests were run on small pieces of membranes using a Clamco Model 250B variable temperature, heat sealer. Copolymer 1 was evaluated with a number of thermoplastic materials at 177° C. Good to excellent seals were obtained with polar materials, such as nylon 66 (sealed at 260° C.), acrylic and Alcryn ® ALX 6387 (thermoplastic elastomer from duPont). Fair adhesion was obtained with the thermoplastic elastomer Santoprene ® 101-73A black. Poor or no adhesion was obtained with the non-polar polystyrene, polypropylene, and a sodium carboxylate polyethylene ionomer or Santoprene ® 101-73A neutral.

Quantitative tests were run on 2.54 cm wide strips. The area of the heat seal was 1.61 cm². The seal (or shear) strength is equal to four times the force required to break the seal. Results are recorded in Table III. A number of heat sealed samples were immersed in water for 7 days. The seals retained essentially all their strength, see Table IV.

EXAMPLE 3. PERMEABILITY TESTING

1. A Ghannam-Chien membrane permeation system was employed to assess the in vitro permeation of progesterone and hydrocortisone through the silicone urethane membranes according to a modification of the method of Tojo[1].

[1] K. Tojo, Y. Sun, M. Ghannam, and Y. W. Chien. Characterization of a Membrane Permeation System for Controlled Drug Delivery Studies AICHE Journal, 31(5), 741-46 (1985).

Progesterone and hydrocortisone were selected as a lipophilic and hydrophilic molecular probe of a steroidal structure, respectively. The permeation system was composed of a donor and receptor compartment in which the fluid is agitated by a matching set of bar shaped magnets. A 200 ml volume of a saturated drug solution employing 40 percent (v/v) of polyethylene glycol 400 (PEG 400) in distilled water was placed in the donor compartment and 200 ml of drug free solvent placed in the receptor compartment. The membrane having a surface area of 13.85 cm² and thickness ranging from 0.25 to 0.63 centimeters was mounted between both cells. The temperature of solution was maintained at 37° C. and agitated at 700 rpm. Permeation studies were conducted over a 24 hour period and aliquots of receptor solution removed at 1, 2, 3, 4, 5, 6, 7, 8, 16 and 24 hours and quantitated for drug content by use of UV spectrophotometry. The steady state permeation rate (flux) was determined by Linear Regression Analysis from the cummulative drug release versus time relationship. The steady state flux corresponds to the slope of the line.

In general progesterone, a lipophilic steroid, possessed a greater normalized flux through the silicone urethane copolymer membranes compared to hydrocortisone, a more hydrophilic steroid (Table V). The permeation rate of each drug could be tailored within a modest range by selection of the appropriate silicone-urethane copolymer or copolymer blends (Table V).

EXAMPLE 4. BIOCOMPATIBILITY TESTING

1. Tissue cell culture: Cytotoxicity Test

The tissue cell culture tests are designed to determine the cytopathic effects (CPE) of a material or its extracts in contact with monolayers of diploid human cells.

No CPE was produced by Copolymer No. 1 in direct contact or by its cell culture medium extract. However, one of the two initial dimethyl sulfoxide (DMSO) extracts produced a CPE. The two subsequent DMSO extracts tested were negative. Therefore, this sample has passed these tissue cell culture tests.

The test material was evaluated for cytotoxicity by placing the material in direct contact with confluent monolayers of human fetal cells for 24 hours. The cytopathic effects of the test material were microscopically compared against a positive and a negative control.

In addition, the test material was extracted using a ratio of 3 cm² of sample surface area to 1 ml extraction medium. The DMSO preparations were autoclaved for one hour at 121° C. and then diluted to 2%. The preparations were incubated at 38° C. for 24 hours. The extracts were tested by aspirating the medium from acceptable wells and replacing it with 1.5 ml of the extract preparations from the test material. After incubation for 24 hours, the cytopathic effects were microscopically evaluated against both a positive and a negative control.

TABLE I

COMPOSITIONS OF HEAT SEALABLE, SILICONE URETHANE COPOLYMERS

| Copolymers | Wt % $H_{12}$MDI | Wt % BD | Wt % PDMS | Wt % PTMO | Wt % PEO |
|---|---|---|---|---|---|
| 1 | 23.85 | 5.36 | 70.79 | 0.00 | 0.00 |
| 2 | 18.21 | 4.10 | 77.69 | 0.00 | 0.00 |
| 3 | 32.61* | 7.83 | 31.85 | 27.72 | 0.00 |
| 4 | 35.74* | 8.58 | 55.68 | 0.00 | 0.00 |
| 5 | 24.44 | 5.50 | 50.32 | 19.74 | 0.00 |
| 6 | 21.03 | 4.73 | 47.70 | 26.54 | 0.00 |
| 7 | 25.74 | 5.79 | 52.98 | 0.00 | 15.49 |
| 8 | 26.83 | 6.04 | 40.31 | 0.00 | 26.81 |
| 9 | 31.95 | 7.19 | 29.21 | 31.65 | 0.00 |
| 10 | 32.25 | 7.25 | 50.42 | 10.08 | 0.00 |
| 11 | 29.12 | 6.54 | 21.81 | 42.53 | 0.00 |

*MDI

TABLE II

MECHANICAL PROPERTIES AND MOLECULAR WEIGHTS OF HEAT SEALABLE, SILICONE URETHANE COPOLYMERS

| Co-polymer | Tensile[1] (MPa) | Elongation (%) | Tear[2] (KN/m) | Durometer[3] (Shore A) | GPC[4] Mw |
|---|---|---|---|---|---|
| 1 | 11.4 | 420 | 33.2 | 85 | 229,000 |
| 2 | 6.9 | 440 | 16.6 | 74 | 267,000 |
| 3 | 26.3 | 570 | 68.2 | 88 | 191,000 |
| 4 | 17.5 | 233 | 110.2 | 96 | 85,700 |
| 5 | 5.9 | 340 | 27.1 | 76 | 153,000 |
| 6 | 7.9 | 300 | 22.8 | 74 | 176,000 |
| 7 | 9.9 | 600 | 26.2 | 82 | 230,000 |
| 8 | 6.9 | 930 | 29.8 | 73 | 178,000 |
| 9 | 40.5 | 540 | 63.0 | 92 | 136,000 |
| 10 | 21.6 | 300 | 82.2 | 94 | 89,800 |
| 11 | 37.2 | 600 | NT[a] | NT | 118,000 |

[1]Tensile strength and elongation were tested in accordance with ASTM D 412-80.
[2]Tear Strength was determined in accordance with ASTM D 624-81.
[3]Durometer was tested in accordance with ASTM D 2240-86.
[4]Gel permeation chomotography (GPC) was run in THF at 2 ml/min using polystyrene calibration standards.
[a]not tested

TABLE III

QUANTITATIVE HEAT SEAL TEST RESULTS OF SILICONE URETHANE COPOLYMERS

| Copolymer | Percent Siloxane | Seal Temp deg. C. | Shear Strength (MPa) against Scotchpak ® 1006 | Scotchpak ® 1012 | Scotchpak ® 1220 | Mylar ® | Polyethylene |
|---|---|---|---|---|---|---|---|
| 1 | 70 | 157 | NT[a] | NT | 0.21 | NT | NT |
| 2 | 78 | 157 | NT | NT | 0.11 | NT | NT |
| 3 | 30 | 177 | 0.33 | NT | NT | 0.32 | NT |
| 4 | 56 | 177 | 0.05 | NT | NT | 0.51 | NT |
| 5 | 50 | 121 | 0.13 | 0.15 | 0.16 | 0.13 | 0.03 |
| 6 | 37.7 | 121 | 0.06 | 0.10 | 0.09 | 0.12 | 0.03 |
| 7 | 53 | 157 | NT | 0.19 | NT | 0.17 | NT |
| 8 | 40 | 113 | NT | 0.16 | 0.12 | 0.15 | NT |
| 8 | 40 | 121 | NT | 0.13 | 0.12 | 0.14 | NT |
| 8 | 40 | 130 | NT | 0.15 | NT | 0.16 | NT |

[a]Not tested (NT)

TABLE IV

SHEAR STRENGTH OF HEAT SEALS OF SILICONE URETHANE COPOLYMERS AFTER 7 DAYS WATER IMMERSION

| Copolymer | Percent Siloxane | Seal Temp. deg. F. | Shear Strength (MPa) against Scotchpak ® 1220 | Mylar ® |
|---|---|---|---|---|
| 7 | 53 | 157 | NT[a] | 0.13 (78%)* |
| 1 | 70 | 157 | 0.24 (116%)* | NT |
| 2 | 78 | 157 | 0.09 (85%)* | NT |

[a]Not tested (NT)
*Percentage of shear strength prior to water soak.

TABLE V

PERMEABILITY OF SELECTED DRUGS THROUGH HEAT SEALABLE SILICONE URETHANE COPOLYMER MEMBRANES

| Copolymer Number | Normalized Permeability (micrograms) (cm)/(cm²)(hr) progesterone | hydrocortisone |
|---|---|---|
| 1 | 0.111 | 0.005 |
| 9 | 0.025 | 0.006 |
| 10 | 0.023 | NT[a] |
| 11 | 0.505 | NT |
| 25/75* | 0.054 | 0.004 |
| 50/50* | 0.042 | 0.004 |
| 75/25* | 0.084 | 0.005 |

[a]Not tested (NT)
*Blends of copolymers 1 and 9 with the first number signifying weight percentage of copolymer 1 and the second number signifying weight percentage of copolymer 9.

That which is claimed is:

1. In a transdermal drug delivery system, comprising in combination:
   (a) an impermeable backing member;
   (b) a release rate controlling membrane heat and pressure sealed to said backing member without the use of a separate adhesive;
   (c) a reservoir positioned between said backing member and said membrane containing a medicinally active ingredient;
   (d) means to attach said system to the skin of a patient;
   said member comprising a substantially linear block copolymer which is a reaction product of a polydiorganosiloxane oligomer which forms soft segments in a said reaction product and a diisocyanate which forms hard segments, said copolymer having a glass transition temperature between 75° C. and 200° C. said soft segments comprising from 60 to 90 percent by weight, based on the weight of said copolymer and said hard segments comprising from about 10 to 40 percent by weight thereof.

2. A device according to claim 1 where said diisocyanate is an aromatic aliphatic or cycloaliphatic diisocyanate.

3. A device according to claim 1 wherein said membrane is in the form of a film having a thickness of from 0.01 to 1 mm.

4. A device according to claim 2 where the organic diisocyanate is p-tolylene diisocyanate, 4,4'-diphenyl methane diisocyanate, isoporone diisocyante, 4,4'-dicyclohexylmethanediisocyanate, or isophorone diisocyanate.

5. A device according to claim 1 wherein said soft blocks also contain from 0 to 70 weight per cent of polyalkylene oxide units based on the weight of said copolymer.

6. A device according to claim 1 wherein molecules of a low molecular weight diol are present in said hard blocks.

7. A device according to claim 1 wherein said polydiorganosiloxane is polydimethylsiloxane.

8. A method for forming a transdermal drug delivery device comprising (A) providing an impermeable backing member, (B) positioning a drug containing reservoir over a central portion of said backing member (C) positioning a rate controlling membrane over said reservoir with the periphery thereof extending beyond the perimeter of said reservoir, said periphery overlying said backing without any separate adhesive therebetween, said rate controlling polymeric material being from 0.01 to 1 mm. thick and permeable to said drug, said polymeric material comprising substantially linear block copolymers comprising from 3 to 40 weight percent of hard segments consisting essentially of polyurethane units derived from an organic diisocyanate and an alkylene diol, and from 60 to 97 weight percent of soft segments comprising at least one polydiorganosiloxane unit, said copolymer having a glass transition temperature between 50° and 200° C., and (D) sealing the periphery of said membrane to said backing by applying heat and pressure thereto.

9. A method according to claim 8 where said hard segment of the copolymer constitutes from 25 to 35 percent by weight of the copolymer, the organic diisocyanate is an aromatic or cycloaliphatic diisocyanate, the polydiorganosiloxane units contain from 20 to 40 diorganosiloxane repeating units and polyethylene oxide units constitute from 15 to 30 percent by weight of said copolymer, and said layer is in the form of a film having a thickness of from 0.1 to 1 mm.

10. A method according to claim 8 where the organic diisocyanate is p-tolylene diisocyanate, 4,4'-diphenylmethanediisocyanate or 4,4'-dicyclohexylmethanediisocyanate, the alkylene diol is 1,4-butanediol, the polydiorganosiloxane units contain from 20 to 40 diorganosiloxane repeating units, and the molar ratio of diisocyanate units to alkylene diol units to the combination of polydiorganosiloxane and polyethylene oxide units is 3:2:1, respectively.

* * * * *